United States Patent [19]

Ravichandran et al.

[11] Patent Number: 5,019,613
[45] Date of Patent: May 28, 1991

[54] N-HYDROCARBYLOXY DERIVATIVES OF HINDERED AMINE-SUBSTITUTED S-TRIAZINES

[75] Inventors: Ramanathan Ravichandran, Nanuet; James P. Galbo, Hartsdale, both of N.Y.

[73] Assignee: Ciba-Geigy Corporation, Ardsley, N.Y.

[21] Appl. No.: 479,907

[22] Filed: Feb. 14, 1990

Related U.S. Application Data

[63] Continuation-in-part of Ser. No. 326,854, Mar. 21, 1989, abandoned.

[51] Int. Cl.$^5$ .................. C08K 5/3435; C07D 403/00
[52] U.S. Cl. .................................... 524/100; 544/198; 544/212
[58] Field of Search ................. 524/100; 544/198, 212

[56] References Cited

U.S. PATENT DOCUMENTS 4,665,185  3/1987  Winter et al. .................. 546/184
4,816,507  3/1989  Cantatore et al. .................. 524/100

FOREIGN PATENT DOCUMENTS 0176106  4/1986  European Pat. Off. ............ 544/198

OTHER PUBLICATIONS

Shylanpintokh et al., "Developments in Polymer Stabilisation", V 41–70 (1982).

Primary Examiner—Kriellion Morgan
Attorney, Agent, or Firm—Luther A. R. Hall

[57] ABSTRACT

N-Hydrocarbyloxy derivatives of poly(2,2,6,6-tetraalkylpiperidin-4-yl) -1,3,5-triazines corresponding to the formulae I, II or III

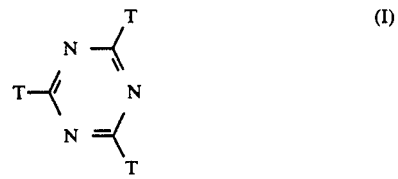

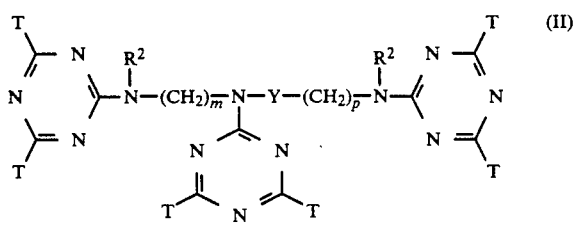

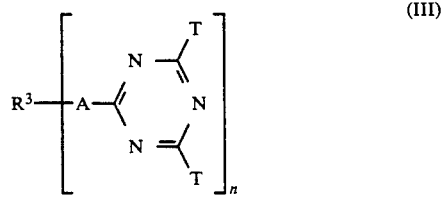

wherein T is

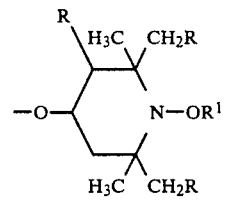

are effective light stabilizers in a wide variety of substrate systems.

21 Claims, No Drawings

N-HYDROCARBYLOXY DERIVATIVES OF HINDERED AMINE-SUBSTITUTED S-TRIAZINES

This is a continuation-in-part of application Ser. No. 326,854, filed on Mar. 21, 1989, now abandoned.

The present invention relates to novel triazine derivatives and the use thereof to stabilize a broad range of substrates against light-induced degradation.

It is known that synthetic polymers undergo progressive changes in their physical properties, such as color change and loss of mechanical properties, when exposed to sunlight or other sources of ultraviolet radiation. A variety of additives have been proposed and utilized to retard the degradation including benzophenones, benzotriazoles, acrylic acid derivatives, oxanilides, aryl-s-triazines, nickel complexes and sterically hindered amines. A representative sampling of the latter has been enumerated in, e.g. U.S. Pat. Nos. 4,344,876, 4,426,471 and 4,426,472, in a coatings stabilization context.

Included among the sterically hindered amines are various (tetraalkyl-4-piperidyl)amino-triazine derivatives. Reference is made to U.S. Pat. Nos. 3,925,376, 4,086,204, 4,108,829, 4,477,615, 4,533,688 and 4,547,548 are representative disclosures in this area. These hindered amine light stabilizers do not possess structures having an 0-substituted moiety substituted directly on the nitrogen atom of the hindered amine.

By the way of disclosure of further hindered amine-substituted triazine derivatives, N-unsubstituted and N-alkyl substituted 2,2,6,6-tetramethylpiperidin-4-yloxy1,3,5-triazines are noted in U.S. Pat. Nos. 4,314,933 and 4,426,471. Additionally, N-alkoxy ($C_1$-$C_{12}$)-2,2,6,6-tetramethylpiperidin-4-yl derivatives of 1,3,5-triazine are generically claimed in U.S. Pat. No. 4,740,544.

The compounds of the instant invention correspond to the formulas I, II or III

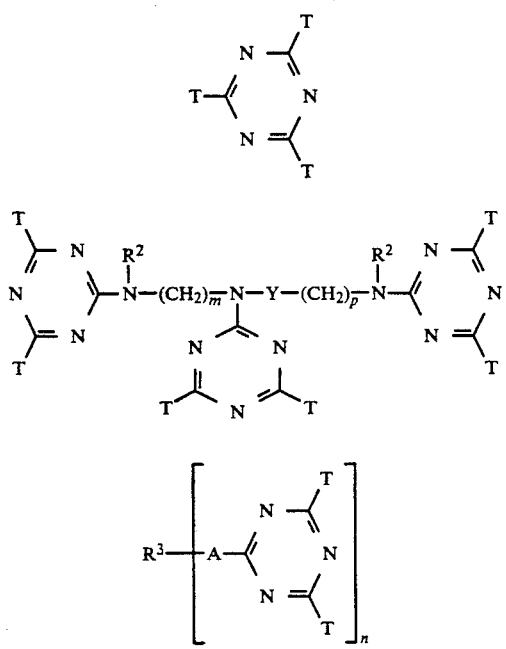

wherein T is

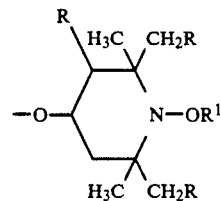

R is hydrogen or methyl;

$R^1$ is $C_1$-$C_{18}$-alkyl, $C_2$-$C_{18}$-alkenyl, $C_2$-$C_{18}$-alkynyl, $C_5$-$C_{12}$-cycloalkyl, $C_5$-$C_{12}$-cycloalkenyl, $C_6$-$C_{10}$-bicycloalkyl, $C_6$-$C_{10}$-aryl, $C_7$-$C_{12}$-aralkyl or $C_7$-$C_{12}$-aralkyl substituted by $C_1$-$C_{12}$-alkyl or $C_6$-$C_{10}$-aryl;

$R^2$ is hydrogen, $C_1$-$C_{12}$-alkyl or

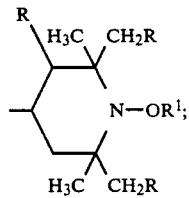

Y is a direct bond or

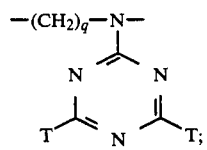

m, p and q are independently 2–6;

A is oxygen, sulfur or -N($R^2$)-;

n is 2–4; and $R^3$ is an n-valent alkane or aryl radical.

Alkyl groups are preferably $C_1$-$C_{12}$ and include methyl, ethyl, propyl, butyl, hexyl, heptyl, octyl, decyl, dodecyl as well as octadecyl. Cycloalkyl is preferably cyclopentyl and cyclohexyl. Alkenyl is preferably vinyl and allyl while alkynyl is preferably propargyl. Aryl is preferably phenyl, naphthyl and tolyl while aralkyl is preferably benzyl, alpha-methylbenzy and alpha,alpha-dimethylbenzyl.

$R^1$ is most preferably methyl, heptyl, octyl and cyclohexyl. $R^2$ is most preferably hydrogen or $C_1$-$C_4$-alkyl and particularly hydrogen or n-butyl.

For compounds of formula II, m, p and q are preferably 2, 3 or 6 with Y being either the direct bond or the substituted triazine.

For compounds of formula III, A is preferably oxygen or —N($R^2$)— with the above identified $R^2$ preferences. When n is 2, $R^3$ is preferably straight chain or branched $C_1$-$C_{12}$-alkylene including methylene, ethylene and hexamethylene, $C_2$-$C_6$-alkylidene, $C_5$-$C_{10}$-cycloalkylene, $C_6$-$C_{10}$-arylene including phenylene, xylylene and naphthylene, or alkylenearylenealkylene of 8 to 10 carbon atoms. A as oxygen with $R^3$ as p-phenylene and A as —NH— with $R^3$ as ethylene or hexamethylene are particularly preferred.

When n is 3, $R^3$ is preferably alkanetriyl of 3 to 6 carbon atoms such as glyceryl or trimethylylpropane, or aryl-triyl of 6 to 10 carbon atoms.

When n is 4, $R^3$ is preferably alkanetetrayl of 4 to 6 carbon atoms such as pentaerythrityl or aryl-tetrayl of 6 to 10 carbon atoms.

Trivalent and tetravalent groups also include

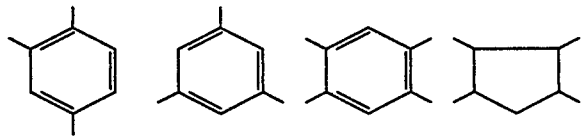

The compounds of the invention can be prepared by reacting cyanuric chloride or derivatives of cyanuric chloride with 4-hydroxy-1-hydrocarbyloxy-2,2,6,6-tetraalkylpiperidines in the presence of an inert solvent such as acetone, methyl ethyl ketone, dioxane, tetrahydrofuran, xylene, and the like, and in the presence of a strong base such as sodium hydride.

U.S. Pat. No. 4,665,185 teaches the preparation of N-hydroxypiperidines by oxidation of the hindered amine with an appropriate peroxy compound such as hydrogen peroxide and a metal oxide catalyst followed by catalytic hydrogenation. The N-hydroxy compounds can be alkylated by reaction with sodium hydride and halogenated hydrocarbons.

The preferred method of making the N-hydrocarbyl compounds involves the thermal reaction of a hydrocarbon solution, especially effective with hydrocarbons such as cyclohexane, heptane, octane, nonane or ethylbenzene, of the hindered amine or its N-oxyl derivative with tert-butyl hydroperoxide and a metal oxide catalyst See copending patent application Ser. Nos. 259,949 and 259,950.

The starting materials needed to prepare these compounds are items of commerce or can be prepared by known methods.

Although the instant application emphasizes the 2,2,6,6-tetraalkylpiperidine structure, it is to be noted that the invention also relates to compounds wherein the following tetraalkyl substituted piperazine or piperazinone moieties are substituted for the above-noted tetraalkylpiperidine moiety:

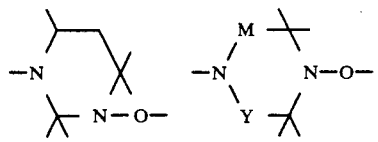

wherein M and Y are independently methylene or carbonyl, preferably M being methylene and Y being carbonyl. It is understood that the identified substituents applicable to such compounds are those which are appropriate for substitution on the ring nitrogen atoms.

Substrates in which the compounds of this invention are particularly useful are polyolefins such as polyethylene and polypropylene; polystyrene, including especially impact polystyrene; ABS resin; elastomers such as e.g. butadiene rubber, EPM, EPDM, SBR and nitrile rubber.

In general polymers which can be stabilized include

1. Polymers of monoolefins and diolefins, for example polyethylene (which optionally can be crosslinked), polypropylene, polyisobutylene, polybutene-1, polymethyl- pentene-1, polyisoprene or polybutadiene, as well as polymers of cycloolefins, for instance of cyclopentene or norbornene.

2. Mixtures of the polymers mentioned under 1), for example mixtures of polypropylene with polyisobutylene.

3. Copolymers of monoolefins and diolefins with each other or with other vinyl monomers, such as, for example, ethylene/propylene, propylene/butene-1, propylene/ isobutylene, ethylene/butene-1, propylene/butadiene, isobutylene/isoprene, ethylene/alkyl acrylates, ethylene/ alkyl methacrylates, ethylene/vinyl acetate or ethylene/ acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or methylstyrene with dienes or acrylic derivatives, such as, for example, styrene/ butadiene, styrene/acrylonitrile, styrene/ethyl methacrylate, styrene/butadiene/ethyl acrylate, styrene/ acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/ propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASAor AES-polymers.

7. Halogen-containing polymers, such as polychloroprene, chlorinated rubbers, chlorinated or sulfochlorinated polyethylene, epichlorohydrine homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/ vinylidene chloride, vinyl chloride/vinyl acetate or vinylidene chloride/vinyl acetate copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under (8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymer).

15 Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane]terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low inflammability.

23. Thermosetting acrylic resins, derived from substituted acrylic esters, such as epoxy-acrylates, urethane-acrylates or silicone-acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene/butadiene copolymers.

30. Polysiloxanes such as the soft, hydrophilic polysiloxanes described, for example, in U.S. Pat. No. 4,259,467; and the hard polyorganosiloxanes described, for example, in U.S. Pat. No. 4,355,147.

31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst 32. Radiation curable compositions containing ethylenically unsaturated monomers or oligomers and a polyunsaturated aliphatic oligomer.

1. 33 Epoxymelamine resins such as light-stable epoxy resins crosslinked by an epoxy functional coetherified high solids melamine resin such as LSE 4103 (Monsanto).

In general, the stabilizers of this invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain various conventional additives, such as the following.

1. Antioxidants 1.1. Alkylated monophenols, for example,
2,6-di-tert.butyl-4-methylphenol
-tert.butyl-4,6-dimethylphenol
2,6-di-tert.butyl-4-ethylphen 1
2,6-di-tert.butyl-4-n-butylphenol
2,6-di-tert.butyl-4-i-butylphenol
2,6-di-cyclopentyl-4-methylphenol
-(α-methylcyclohexyl)-4,6-dimethylphenol
2,6-di-octadecyl-4-methylphenol
2,4,6-tri-cyclohexylphenol
2,6-di-tert.butyl-4-methoxymethylphenol 1.2. Alkylated hydroquinones, for example,
2,6-di-tert.butyl-4-methoxyphenol
2,5-di-tert.butyl-hydroquinone
2,5-di-tert.amyl-hydroquinone
2,6-diphenyl-4-octadecyloxyphenol 3. Hydroxylated thiodiphenyl ethers, for example
2,2'-thio-bis-(6-tert.butyl-4-methylphenol)
2,2'-thio-bis-(4-octylphenol)
4,4'-thio-bis-(6-tert.butyl-3-methylphenol)
4,4'-thio-bis-(6-tert.butyl-2-methylphenol)

1.4. Alkylidene-bisphenols, for example,
2,2'-methylene-bis-(6-tert.butyl-4-methylphenol)

2,2'-methylene-bis-(6-tert butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert.butylphenol)
2,2'-ethylidene-bis-(4,6-di-tert.butylphenol)
2,2'-ethylidene-bis-(6-tert.butyl-4-isobutylphenol)
4,4'-methylene-bis-(2,6-di-tert.butylphenol)
4,4'-methylene-bis-(6-tert.butyl-2-methylphenol)
1,1-bis-(5-tert.butyl-4-hydroxy-2-methylphenyl-butane
2,6-di-(3-tert.butyl-5-methyl-2-hydroxybenzyl)-4-methylphenol
1,1,3-tris-(5-tert.butyl-4-hydroxy-2-methylphenyl)-butane
1,1-bis-(5-tert.butyl-4-hydroxy-2-methylphenyl)-3-n-dodecylmercaptobutane
ethyleneglycol-bis-[3,3-bis-(3'-tert.butyl-4'-hydroxyphenyl)-butyrate]
di-(3-tert.butyl-4-hydroxy-5-methylphenyl)-dicyclopentadiene
di-[2-(3'-tert.butyl-2'-hydroxy-5'-methyl-benzyl)-6-tert.butyl-4-methylphenyl]-terephthalate.

1.5. Benzyl compounds, for example,
1,3,5-tri-(3,5-di-tert.butyl-4-hydroxybenzyl)-2,4,6trimethylbenzene-di-(3,5-di-tert.butyl4-hydroxybenzyl)-sulfide
3,5-di-tert.butyl-4-hydroxybenzyl-mercapto-acetic acid isooctyl ester
bis-(4-tert.butyl-3-hydroxy-2,6-dimethylbenzyl)dithiolterephthalate
1,3,5-tris-(3,5-di-tert.butyl-4-hydroxybenzyl)-isocyanurate
1,3,5-tris-(4-tert.butyl-3-hydroxy-2,6-dimethylbenzyl)isocyanurate
3,5-di-tert.butyl-4-hydroxybenzyl-phosphoric acid-diocta decyl ester
3,5-di-tert.butyl-4-hydroxybenzyl-phosphoric acid-monoethyl ester, calcium-salt 1.6. Acylaminophenols, for example,
4-hydroxy-lauric acid anilide
4-hydroxy-stearic acid anilide
2,4-bis-octylmercapto-6-(3,5-tert.butyl-4-hydroxyanilino)s-triazine
octyl-N-(3,5-di-tert.butyl-4-hydroxyphenyl)-carbamate 1.7. Esters of β-(3,5-di-tert.butyl-4-hydroxyphenyl)-propionic acid with monohydric or polyhydric alcohols, for example,

| methanol | diethyleneglycol |
| octadecanol | triethyleneglycol |
| 1,6-hexanediol | pentaerythritol |
| neopentylglycol | tris-hydroxyethyl isocyanurate |
| thiodiethyleneglycol | di-hydroxyethyl oxalic acid diamide |

1.8. Esters of β-(5-tert.butyl-4-hydroxy-3-methylphenyl)propionic acid with monohydric or polyhydric alcohols, fr example,

| methanol | diethyleneglycol |
| octadecanol | triethyleneglycol |
| 1,6-hexanediol | pentaerythritol |
| neopentylglycol | tris-hydroxyethyl isocyanurate |
| thiodiethyleneglycol | di-hydroxyethyl oxalic acid diamide |

1.9. Amides of β-(3,5-di-tert.butyl-4-hydroxyphenyl)-propionic acid for example,
N,N'-di-(3,5-di-tert.butyl-4-hydroxyphenylpropionyl)hexamethylendiamine
N,N'-di-(3,5-di-tert.butyl-4-hydroxyphenylpropionyl)trimethylendiamine
N,N'-di-(3,5-di-tert.butyl-4-hydroxyphenylpropionyl)hydrazine 2. UV absorbers and light stabilizers 2.1. 2-(2'-Hydroxyphenyl)-benzotriazoles, for example, the 5'-methyl-, 3',5'-di-tert-butyl-, 5'-tert-butyl 5'-(1,1,3,3-tetramethylbutyl)-, 5-chloro-3',5'-di-tertbutyl-, 5-chloro-3'-tert-butyl-5'-methyl-, 3'-sec-butyl-5'-tert-butyl-, 4'-octoxy, 3',5'-di-tert-amyl- 3',5'-bis-(α,α-dimethylbenzyl), 3'-tert-butyl-5'-(2-(omega-hydroxyocta-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives 2.2. 2-Hydroxy-benzophenones, for example, the 4-hydroxy-, 4-methoxy-, 4-octoxy, 4-decyloxy- 4-dodecyloxy- 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate octylphenyl salicylate, dibenzoylresorcinol, bis-(4-tert-butylbenzoyl)-resorcinol, benzoylresorcinol 3,5-di-tert-butyl-4-hydroxybenzoid acid 2 4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxycinnamic acid methyl ester, N-(β-carbomethoxy-β-cyanovinyl)-2-methyl-indoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris(2,2,6,6-tetramethylpiperidyl)-nitrilotriacetate, tetrakis-(2,2,6,6-tetramethyl-4-piperidyl)-1,2,3,4-butanetetracarbonic acid, 1,1'(1,2-ethanediyl)-bis-(3,3,5,5tetramethylpiperazinone).

2.7. Oxalic acid diamides, for example, 4,4'-dioctyloxyoxanilide, 2,2'-di-octyloxy-5,5'-di-tert-butyl-oxanilide 2,2'-di-dodecyloxy-5,5'-ditert-butyl-oxanilide, 2-ethoxy-2'-ethyl-oxanilide, N,N'-bis (3-dimethylaminopropyl)oxalamide, 2-ethoxy-5-tert-butyl-2'-ethyloxanilide, and its mixture with 2-ethoxy-2'-ethyl-5,4'-di-tert-butyloxanilide and mixtures of ortho- and para-methoxy-as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-striazine; 2,4-bis(2,4-dihydroxyphenyl)-6-(4-chlorophenyl)- s-triazine; 2,4-bis[2-hydroxy-4-(2-hydroxyethoxy)phenyl]-6(4-chlorophenyl)-s-triazine; 2,4-bis[2-hydroxy-4-(2-hydroxyethoxy)phenyl]-6-phenyl-s-triazine; 2,4-bis[2-hydroxy-4-(2-hydroxyethoxy)-phenyl]-6-(2,4-dimethylphenyl)-s-triazine; 2,4-bis[2-hydroxy-4-(2-hydroxyethoxy)phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl4-hydroxyphenylpropionyl)-hydrazine, 3-salicyloylamino1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-ditertbutylphenyl)pentaerythritol diphosphite, tristearylsorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Polyamide stabilizers, for example copper salts in combination with iodides and/or phosphorus compounds and salts of divalent manganese.

8. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

9. Nucleating agents, for example, 4-tert-butyl-benzoic acid, adipic acid, diphenylacetic acid.

10. Fillers and reinforcing agents, for example, calcium carbonate, silicates, glass fibers, asbestos, talc, kaolin, mica, barium sulfate, metal oxides and hydroxides, carbon black, graphite.

11. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

Of particular interest is the utilization of the instant derivatives in a variety of coating systems including ambient cured and acid catalyzed coating systems. In particular, the physical integrity of the coatings is maintained to a higher degree with significant reduction in loss of gloss and yellowing Key improvements include the substantial absence of the cure retardation encountered with N-alkyl hindered amine light stabilizers; the substantial absence of flocculation and dispersion destabilization seen when N-alkyl hindered amines are utilized in certain pigmented coating systems and the absence of adhesion loss between the coating and polycarbonate substrate. Accordingly, the present invention also relates to the use of the instant compounds, optionally together with further stabilizers, for stabilizing ambient cured coatings based on alkyd resins; thermoplastic acrylic resins; acrylic alkyds; acrylic alkyd or polyester resins optionally modified with silicon, isocyanates, isocyanurates, ketimines or oxazolidines; and epoxide resins crosslinked with carboxylic acids, anhydrides, polyamines or mercaptans; and acrylic and polyester resin systems modified with reactive groups in the backbone thereof and crosslinked with epoxides; against the degradative effects of light, moisture and oxygen.

Furthermore, in their industrial uses, enamels with high solids content based on crosslinkable acrylic, polyester, urethane or alkyd resins are cured with an additional acid catalyst. Light stabilizers containing a basic nitrogen group are generally less than satisfactory in this application. Formation of a salt between the acid catalyst and the light stabilizer leads to incompatibility or insolubility and precipitation of the salt and to a reduced level of cure and to reduced light protective action and poor resistance to moisture.

These acid catalyzed stoving lacquers are based on hot crosslinkable acrylic, polyester, polyurethane, polyamide or alkyd resins. The acrylic resin lacquers, which can be stabilized against light, moisture and oxygen in accordance with the invention, are the conventional acrylic resin stoving lacquers or thermosetting resins including acrylic/melamine systems which are described, for example, in H. Kittel's "Lehrbuch der Lacke und Beschichtungen", Vol. 1 Par 2, on pages 735 and 742 (Berlin 1972), "Lackkunstharze" (1977), by H. Wagner and H. F. Sarx, on pages 229–238, and in S. Paul's "Surface Coatings: Science and Technology" (1985).

The polyester lacquers, which can be stabilized against the action of light and moisture, are the conventional stoving lacquers described e.g. in H. Wagner and H. F. Sarx, op. cit., on pages 86–99.

The alkyd resin lacquers which can be stabilized against the action of light and moisture in accordance with the invention, are the conventional stoving lacquers which are used in particular for coating automobiles (automobile finishinq lacquers), for example lacquers based on alkyd/ melamine resins and alkyd/acrylic/melamine resins (see H. Wagner and H. F. Sarx, op. cit., pages 99–123). Other crosslinking agents include glycoluril resins, blocked isocyanates or epoxy resins.

The acid catalyzed stoving lacquers stabilized in accordance with the invention are suitable both for metal finish coatings and solid shade finishes, especially in the case of retouching finishes, as well as various coil coating applications. The lacquers stabilized in accordance with the invention are preferably applied in the conventional manner by two methods, either by the singlecoat method or by the two-coat method. In the latter method, the pigment-containing base coat is applied first and then a covering coat of clear lacquer over it.

It is also to be noted that the instant substituted hindered amines are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional crosslinkers such as acids, acid anhydrides, amines, and the like.

Correspondingly, the epoxide may be utilized as the crosslinking agent for various acrylic or polyester resin systems that have been modified by the presence of reactive groups on the backbone structure.

To attain maximum light stability in such coatings, the concurrent use of other conventional light stabilizers can be advantageous. Examples are the aforementioned UV absorbers of the benzophenone, benzotriazole, acrylic acid derivative, or oxanilide type, or aryl-s-triazines or metal-containing light stabilizers, for example organic nickel compounds. In two-coat systems, these additional light stabilizers can be added to the clear coat and/or the pigmented base coat.

If such combinations are employed, the sum of all light stabilizers is 0.2 to 20% by weight, preferably 0.5 to 5% by weight, based on the film-forming resin.

Examples of different classes of UV absorbers which may be used in the instant compositions in conjunction with the aforementioned piperidine compounds are referenced in a paper by H. J. Heller in European Polymer Journal Supplement, 1969, pp. 105-132. These classes include the phenyl salicylates, the o-hydroxybenzophenones, the hydroxyxanthones, the benzoxazoles, the benzimidazoles, the oxadiazoles, the triazoles, the pyrimidines, the chinazolines, the s-triazines, the hydroxyphenyl-benzotriazoles, the alpha-cyanoacrylates and the benzoates.

Types of UV absorbers of especial importance are:

(a) 2-(2'-Hydroxyphenyl)-benzotriazoles, for example the 5'-methyl-, 3',5'-di-tert-butyl- 5'-tert-butyl 5'-(1,1,3,3-tetramethylbutyl)-, 5-chloro-3',5'-di-tert-butyl-,5-chloro-3'-tert-butyl-5'-methyl-, 3'-sec-butyl-5'-tertbutyl-, 4'-octoxy-, and 3',5'di-tert-amyl derivativs.

(b) 2-Hydroxy-benzophenones, for example, the 4-hydroxy-, 4-methoxy-, 4-octoxy-, 4-decyloxy-, 4-dodecyloxy-, 4-benzyloxy, 4,2',4'-trihydroxy- and 2'-hydroxy-4,4'dimethoxy derivativs.

(c) Acrylates, for example, alpha-cyano-β,β-diphenylacrylic acid ethyl ester or isoctyl ester, alpha-carbomethoxy-cinnamic acid methyl ester, alpha-cyano-β-methyl-pmethoxy-cinnamic acid methyl ester or butyl ester, alphacarbomethoxy-p-methoxy-cinnamic acid methyl ester, N-(βcarbomethoxy-β-cyanovinyl)-2-methyl-indoline.

(d) Nickel compounds, for example, nickel complexes of 2,2'-thiobis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2hydroxy4-methyl-phenyl undecyl ketoxime, nickel complexes of 1-phenyl-4-lauroyl-5-hydroxy-pyrazol, optionally with additional ligands.

(e) Oxalic acid diamides, for example 4,4'-di-octyloxyoxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis-(3-dimethylaminopropyl) -oxalamide, 2-ethoxy-5-tert-butyl-2'-ethyloxanilide and its mixture with 2-ethoxy-2'-ethyl-5,4'-di-tert-butyloxanilide and its mixtures of ortho- and para-methoxy- as well as of o- and p-ethoxy-disubstituted oxanilides.

(f) Hydroxyphenyl-s-triazines such as 2,6-bis(2,4-dimethylphenyl)-4-(2-hydroxy-4-octyloxyphenyl)-s-triazine or the corresponding 4-(2,4-dihydroxyphenyl) derivative.

Of particular value in the instant compositions are the benzotriazoles of high molecular weight and low volatility such as 2-[2-hydroxy-3,5-di(alpha,alpha-dimethylbenzyl)-phenyl]-2H-benzotriazole, 2-(2-hydroxy-3,5-di-tert-octylphenyl)-2H-benzotriazole, 2-(2-hydroxy-3-alpha,alkpha-dimethylbenzyl-5-tert-octyl-phenyl)-2H-benzotriazole, 2-(2-hydroxy-3-tert-octyl-5-alpha,alpha-dimethylbenzylphenyl)-2H-benzotriazole, 2-(2-hydroxy-3,5-di-tertamylphenyl)-2H-benzotriazole, 2-[2-hydroxy-3-tert-butyl-5-(2-(omega-hydroxy-octa-(ethyleneoxy)carbonyl)-ethylphenyl] 2H-benzotriazole, dodecylated 2-(2-hydroxy-5-methylphenyl)2H-benzotriazole, 2-[2-hydroxy-3-tert-butyl-5-(2-octyloxycarbonyl)ethylphenyl]-2H-benzotriazole and the 5-chloro compounds corresonding to each of the above named benzotriazoles.

Most preferably the benzotriazoles useful in the instant compositions are 2-[2-hydroxy-3,5-di(alpha,alpha-dimethyl-benzyl)phenyl]-2H-benzotriazole, dodecylated 2-(2- hydroxy-5-methylphenyl)-2H-benzotriazole, 2-[2-hydroxy-3-tert-butyl-5-(2-(omega-hydroxy-octa-(ethyleneoxy) carbonyl)-ethylphenyl]-2H-benzotriazole, 2-[2-hydroxy-3-tert-butyl-5-(2-octyloxycarbonyl)ethylphenyl]-2H-benzotriazole and 5-chloro-2-[2-hydroxy-3-tert-butyl-5-(2-octyloxycarbonyl)ethylphenyl]-2H-benzotriazole.

It is also contemplated that the instant compounds will be particularly effective as stabilizers for polyolefin fibers, especially polypropylene fibers, when used in conjunction with other stabilizers selected from the group consisting of the phenolic antioxidants, hindered amine light stabilizers, organic phosphorus compounds, ultraviolet absorbers and mixtures thereof.

A preferred embodiment of the instant invention pertains to stabilized compositions comprising
(a) an acid catalyzed thermoset coating or enamel based on hot crosslinkable acrylic, polyester or alkyd resins,
(b) a NO-$R^1$-substituted 2,2,6,6-tetralkylpiperidine compound, and
(c) a UV absorber selected from the group consisting of the benzophenones, benzotriazoles, acrylic acid derivatives, organic nickel compounds, aryl-s-triazines and oxanilides Further ingredients which the enamels or coatings can contain are antioxidants, for example those of the sterically hindered phenol derivatives, phosphorus compounds, such as phosphites, phosphines or phosphonites, plasticizers, levelling assistants, hardening catalysts, thickeners, dispersants or adhesion promoters.

A further preferred embodiment of the instant invention is a stabilized composition containing components (a), (b) and (c) described above which additionally contains as component (d) a phosphite or phosphonite.

The amount of phosphite or phosphonite (d) which is used in the instant compositions is from 0.05 to 2% by weight, preferably from 0.1 to 1% by weight, based on the film forming resin In two-coat systems, these stabilizers may be added to the clear coat and/or base coat.

Typical phosphite and phosphonites include triphenyl phosphite, diphenylalkyl phosphites, phenyldialkyl phosphites, tri-(nonylphenyl)phosphite, trilauryl phosphite trioctadecyl phosphite, di-stearyl-pentaerythritol diphosphite, tris-(2,4-di-tert.butylphenyl) phosphite, diisodecylpentaerythritol diphosphite, di-(2,4-di-tert.butylphenyl)pentaerythritol diphosphite, tristearylsorbitol triphosphite, tetrakis-(2,4-di-tert.butylphenyl)-4,4'-diphenylenediphosphonite.

The acid catalyzed thermoset enamels must be stabilized in order to function acceptably in end-use applications. The stabilizers used are hindered amines, preferably those substituted on the N-atom by an inert blocking group in order to prevent precipitation of the basic amine stabilized with the acid catalyst with a concomitant retardation in cure, optionally in combination with UV absorbers, such as the benzotriazoles, benzophenones, substituted s-triazines, phenyl benzoates or oxanilides.

The stabilizers are needed to impart greater retention of durability to the cured enamels (as measured by 20° gloss, distinction of image, cracking or chalking); the stabilizers must not retard cure (normal bake for auto finishes at 121° C. and low bake repair at 82° C. (as measured by hardness, adhesion, solvent resistance and humidity resistance), the enamel should not yellow on curing and further color change on exposure to light should be minimized; the stabilizers should be soluble in the organic solvents normally used in coating applications such as methyl amyl ketone, xylene, n-hexyl acetate, alcohol and the like.

The instant hindered amine light stabilizers substituted on the N-atom by an O-substituted moiety fulfill each of these requirements and provide alone or in combination with a UV-absorber outstanding light stabilization protection to the cured acid catalyzed thermoset enamels.

Still another preferred combination of the instant stabilizers is with a hydroxylamine in order to protect polypropylene fibers from gas fading.

The following examples are presented for the purpose of illustration only and are not to be construed to limit the nature or scope of the instant invention in any manner whatsoever.

EXAMPLE 1

2,4,6-Tris(1-cyclohexyloxy-2,2,6,6-tetramethylpiperidin-4-yloxy)-1,3,5-triazine

A mixture of 30.0 g (0.117 mol) of 1-cyclohexyloxy-4-hydroxy-2,2,6,6-tetramethylpiperidine, 2.8 g (0.117 mol) of sodium hydride, a few drops of dimethyl sulfoxide, and 150 ml of 1,4-dioxane is heated at reflux for two hours, then allowed to cool. To this mixture is added over 15 minutes solution of 7.2 g (0.039 mol) of cyanuric chloride in 50 ml of dioxane. Salt formation is observed, and the reaction temperature rises from 20° C to 50° C during the addition. The reaction mixture is then heated at reflux for 30 minute and stirred overnight at room temperature. Salts are removed by filtration, and the salt cake is slurried in water and filtered to remove salt from the product, a solid. The crude product is dissolved in boiling methanol and residual salt is removed by filtration. Additional product is recovered from the dioxane filtration. Crude solids are combined and heated in refluxing 2-propanol. Th resulting suspension is allowed to cool, and the solid is isolated by filtration to afford 19.4 g (59% yield) of the title compound, a white solid, m.p. 242°-5° C. (dec.).

Anal. Calcd. for $C_{48}H_{84}N_6O_6$: C, 68.5; H, 10.1; N, 10.0.

Found: C, 68.6; H, 9.9; N, 10.0.

EXAMPLE 2

2,4,6-Tris(1-methoxy-2,2,6,6-tetramethylpiperidin-4-yloxy)-1,3,5-triazine

The title compound is prepared by the reaction of 4-hydroxy-1-methoxy-2,2,6,6-tetramethylpiperidine, sodium hydride, and cyanuric chloride in 1,4-dioxane solvent.

EXAMPLE 3

2,4,6-Tris(1-octyloxy-2,2,6,6-tetramethylpiperidin-4-yloxy)1,3,5-triazine

The title compound is prepared by the reaction of 4-hydroxy-1-octyloxy-2,2,6,6-tetramethylpiperidine, sodium hydride, and cyanuric chloride in 1,4-dioxane solvent.

EXAMPLE 4

N,N'-Dimethyl-N,N'-bis[2,4-bis(1-cyclohexyloxy-2,2,6,6-tetramethylpiperidin-4-yloxy)-1,3,5-triazin-6-yl]-1,6-hexanediamine A mixture of 22.6 g (88.6 mmol) of 1-cyclohexyloxy-4-hydroxy-2,2,6,6-tetramethylpiperidine, 2.13 g (88.6 mmol) of sodium hydride, and 150 ml of 1,4-dioxane is heated at reflux for 2.5 hours. The reaction mixture is cooled to 60° C. and treated with a solution of 7.8 g (17.7 mmol) of N,N'-dimethyl-N,N'-bis(2,4-dichloro-1,3,5-triazin-6-yl)-1,6-hexanediamine in 50 ml of dioxane. The reaction mixture is quenched with ice. The supernatant liquid is decanted, and the residue is dissolved in ethyl acetate (250 ml). The solution is dried over anhydrous magnesium sulfate and concentrated to a glass. Purification by passage through a short column of silica gel with 4:1 hexane:ethyl acetate as the eluent affords 19.8 g (85% yield) of the title compound, a white glass.

Anal. Calcd. for $C_{74}H_{130}N_{12}O_8$: C, 67.5; H, 10.0; N, 12.8.

Found: C, 67.6; H, 10.3; N, 12.4.

EXAMPLE 5

1,2-Bis{[2,4-bis(1-cyclohexyloxy-2,2,6,6-tetramethylpiperidin-4-yloxy-1,3,5-triazin-6-yl]thio}ethane The title compound is prepared by substituting 1,2-bis[(2,4-dichloro-1,3,5-triazin-6-yl)thio]ethane for N,N'-dimethyl-N,N'-bis(2,4-dichloro-1,3,5-triazin-6-yl)-1,6-hexanediamine in Example 4.

Summarizing, this invention is seen to provide a series of new hindered-amine substituted triazine derivatives. Variations may be made in proportions, procedures and materials without departing from the scope of the invention as defined by the following claims.

EXAMPLE 6

Stabilization of High Solids Thermoset Acrylic Resin

Enamel weight of 2-hydroxyethyl acrylate, butyl acrylate, methyl methacrylate, styrene and acrylic acid and of 30% by weight of a melamine resin in the presence of an acid catalyst, p-toluenesulfonic acid, dinonylnaphthalene disulfonic acid or dodecylbenzenesulfonic acid, is formulated to include 2% by weight based on the resin solids of a benzotriazole ultraviolet absorber and an effective stabilizing amount of the test hindered amine light stabilizer.

Commercially available epoxy primed 4"×12" (10.16 cm×30.48 cm) panels (Uniprime from Advanced Coatings Technology) are spray coated with a silver metallic basecoat to a thickness of about 0.8 mil (0.023 mm) and air dried for 3 minutes. The stabilized thermoset acrylic resin enamel is then sprayed onto the basecoated panel to a thickness of about 1.7 mil (0.049 mm). After 15 minutes air-drying, the coated sheets are baked for 30 minutes at 250° F. (121° C.).

After storage for 1 week in a air-conditioned room, the coated panels are subjected to weathering in a QUV exposure apparatus according to test method ASTM G-53/77. In this test, the samples are subjected to weathering in repeated cycles for 4 hours in a humid atmosphere at 50° C. and then for 8 hours under UV light at 70° C. The panels are exposed in the QUV for 1500 hours The 20° gloss values of the panels are determined before and after exposure.

The loss of gloss of the stabilized panels is considerably less than that of the unstabilized control panels.

EXAMPLE 7

Light Stabilization of Polypropylene

This example illustrates the light stabilizing effectiveness of instant stabilizers.

Polypropylene powder (Himont Profax 6501) stabilized with 0 2% by weight of n-octadecyl 3,5-di-tert-butyl-4-hydroxyhydrocinnamate is thoroughly blended with the indicated amount of additive. The blended materials are then milled on a two-roll mill at 182° C. for five minutes after wbich time the stabilized polypropyl is sheeted from the mill and allowed to cool. The milled polypropylene is then cut into pieces and compression molded on a hydraulic press at 250° C. and 175 psi (1.2×106 Pa) into 5 mil (0.127 mm) films. The sample is exposed in a fluorescent sunlight/black light chamber until failure. Failure is taken as the hours required to reach 0 5 carbonyl absorbance by infrared spectroscopy on the exposed films.

The time to failure for a polypropylene composition containing an instant compound as stabilizer is far longer than the time to failure for polypropylene having no such stabilizer present.

What is claimed is:

1. A compound corresponding to the formulae I, II or III

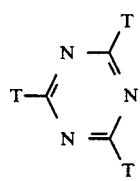
(I)

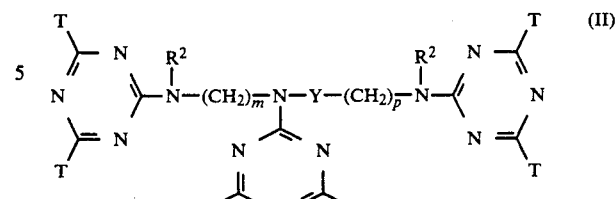
(II)

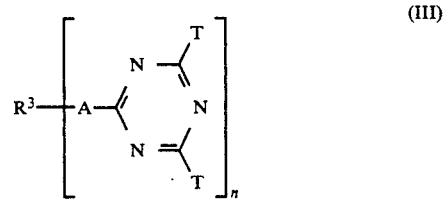
(III)

wherein T is

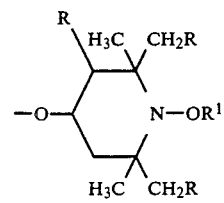

R is hydrogen or methyl;
$R^1$ is $C_1$-$C_{18}$-alkyl, $C_2$-$C_{18}$-alkeny, $C_2$-$C_{18}$-alkynyl, $C_5$-$C_{12}$-cycloalkyl, $C_5$-$C_{12}$-cycloalkenyl, $C_6$-$C_{10}$-bicycloalkyl, $C_6$-$C_{10}$-aryl, $C_7$-$C_{12}$-aralkyl or $C_7$-$C_{12}$-aralkyl substituted by $C_1$-$C_{12}$-alkyl or $C_6$-$C_{10}$aryl;
$R^2$ is hydrogen, $C_1$-$C_{12}$-alkyl or

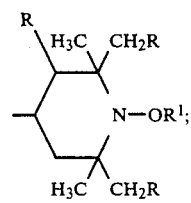

Y is a direct bond or

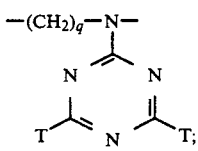

m, p and q are independently 2-6;
A is oxygen, sulfur or —N($R^2$)—;
n is 2-4; and
$R^3$ is an n-valent alkane or aryl radical.

2. A compound of claim 1, wherein $R^1$ is $C_1$-$C_{12}$-alkyl, $C_5$-$C_6$-cycloalkyl, phenyl, naphthyl, tolyl, benzyl, alpha-methylbenzyl or alkpha,alpha-dimethylbenzyl.

3. A compound of claim 2, wherein $R^1$ is methyl, heptyl, octyl or cyclohexyl.

4. A compound of claim 1 corresponding to formula (I) wherein $R^1$ is methyl, heptyl, octyl or cyclohexyl.

5. A compound of claim 1 corresponding to formula (II), wherein Y is a direct bond and m and p are 2, 3 or 6.

6. A compound of claim 1 corresponding to formula (II), wherein Y is the substituted triazine and m, p and q are 2, 3 or 6.

7. A compound of claim 1 corresponding to formula (III), wherein n is 2 and $R^3$ is $C_1-C_{12}$-alkylene, $C_2-C_6$alkylidene, $C_5-C_{10}$-cycloalkylene, $C_6-C_{10}$-arylene or $C_8-C_{10}$-alkylenearylenealkylene.

8. A compound of claim 7, wherein A is oxygen and $R^3$ is p-phenylene.

9. A compound of claim 7, wherein A is —NH— and $R^3$ is ethylene or hexamethylene.

10. A compound of claim 1 according to formula (III), wherein n is 3 and $R^3$ is $C_3-C_6$-alkanetriyl or $C_6-C_{10}$aryl-triyl.

11. A compound of claim 1 according to formula (III), wherein n is 4 and $R^3$ is $C_4-C_6$-alkanetetrayl or $C_6-C_{10}$-aryl-tetrayl.

12. 2,4,6-Tris(1-cyclohexyloxy-2,2,6,6-tetramethylpiperidin-4-yloxy)-1,3,5-triazine according to claim 3.

13. 2,4,6-Tris(1-methoxy-2,2,6,6-tetramethylpiperidin4-yloxy)-1,3,5-triazine according to claim 3.

14. 2,4,6-Tris(1-oxtyloxy-2,2,6,6-tetramethylpiperidin-4-yloxy)-1,3,5-triazine according to claim 3.

15. N,N'Dimethyl-N,N'-bis[2,4-bis(1-cyclohexyloxy2,2,6,6-tetramethylpiperidin-4-yloxy)-1,3,5-triazin-6-yl]1,6-hexanediamine according to claim 7.

16. 1,2-Bis{[2,4-bis(1-cyclohexyloxy-2,2,6,6-tetramethylpiperidin-4-yloxy)-1,3,5-triazin-6-yl]thio}ethane according to claim 7.

17. A composition of matter stabilized against oxidative, thermal or actinic degradation comprising
(a) a synthetic polymer subject to oxidative, thermal or actinic degradation, and
(b) an effective stabilizing amount of a compound according to claim 1.

18. A composition of claim 17, wherein the synthetic polymer is a polyolefin homopolymer or copolymer.

19. A composition of claim 17, wherein said synthetic polymer is a coating system based on alkyd, acrylic, acrylic alkyd, polyester, epoxide, urethane, polyamide, vinyl or epoxy-polyester resins.

20. A composition of claim 20 which contains a UV absorber or additional light stabilizer.

21. A method for stabilizing a synthetic polymer against oxidative, thermal or actinic degradation which comprises incorporating into said organic material an effective stabilizing amount of a compound according to claim 1.

* * * * *